(12) United States Patent
Wu et al.

(10) Patent No.: US 8,611,627 B2
(45) Date of Patent: Dec. 17, 2013

(54) CT SPECTRAL CALIBRATION

(75) Inventors: Xiaoye Wu, Rexford, NY (US); Robert Franklin Senzig, Germantown, WI (US); Jing Zhao, Beijing (CN)

(73) Assignee: General Electric Company, Schenectady, NY (US)

( * ) Notice: Subject to any disclaimer, the term of this patent is extended or adjusted under 35 U.S.C. 154(b) by 428 days.

(21) Appl. No.: 12/976,785

(22) Filed: Dec. 22, 2010

(65) Prior Publication Data

US 2011/0249879 A1 Oct. 13, 2011

Related U.S. Application Data

(60) Provisional application No. 61/289,828, filed on Dec. 23, 2009.

(51) Int. Cl.
*G06K 9/00* (2006.01)
(52) U.S. Cl.
USPC .......................................................... 382/131
(58) Field of Classification Search
None
See application file for complete search history.

(56) References Cited

U.S. PATENT DOCUMENTS

| | | | |
|---|---|---|---|
| 5,359,638 A | 10/1994 | Hsieh et al. | |
| 5,668,846 A | 9/1997 | Fox et al. | |
| 5,907,593 A | 5/1999 | Hsieh et al. | |
| 6,023,494 A | 2/2000 | Senzig et al. | |
| 6,115,487 A * | 9/2000 | Toth et al. | 382/131 |
| 6,198,791 B1 | 3/2001 | He et al. | |
| 6,275,560 B1 | 8/2001 | Blake et al. | |
| 6,285,741 B1 | 9/2001 | Ackelsberg et al. | |
| 6,304,625 B1 | 10/2001 | Senzig et al. | |
| 6,385,277 B1 | 5/2002 | Li et al. | |
| 6,389,096 B1 | 5/2002 | Hoffman et al. | |
| 6,393,090 B1 | 5/2002 | Hsieh et al. | |
| 6,421,412 B1 | 7/2002 | Hsieh et al. | |
| 6,650,928 B1 | 11/2003 | Gailly et al. | |
| 6,661,866 B1 | 12/2003 | Limkeman et al. | |
| 6,801,594 B1 | 10/2004 | Hsieh et al. | |
| 6,810,102 B2 | 10/2004 | Hsieh et al. | |
| 6,816,567 B2 | 11/2004 | Drummond | |
| 6,836,528 B2 | 12/2004 | Reddy et al. | |
| 6,848,827 B2 | 2/2005 | Wu et al. | |
| 6,904,118 B2 | 6/2005 | Wu et al. | |
| 6,904,120 B2 | 6/2005 | Wu et al. | |
| 6,904,127 B2 | 6/2005 | Toth et al. | |
| 6,947,584 B1 | 9/2005 | Avila et al. | |
| 7,006,592 B2 | 2/2006 | Ali et al. | |
| 7,016,457 B1 | 3/2006 | Senzig et al. | |
| 7,031,425 B2 | 4/2006 | Hsieh et al. | |
| 7,031,426 B2 | 4/2006 | Iatron et al. | |
| 7,086,780 B2 | 8/2006 | Wu et al. | |
| 7,139,000 B2 | 11/2006 | Doan et al. | |
| 7,177,453 B2 | 2/2007 | Suryanarayanan et al. | |
| 7,211,046 B2 | 5/2007 | Deller et al. | |
| 7,260,172 B2 | 8/2007 | Arenson et al. | |
| 7,260,174 B2 | 8/2007 | Hoffman et al. | |

(Continued)

*Primary Examiner* — Claire X Wang
(74) *Attorney, Agent, or Firm* — Fletcher Yoder, P.C.

(57) ABSTRACT

The present disclosure relates to the performing spectral calibration of a CT imaging system. In accordance with certain embodiments, spectral calibration phantoms are scanned while positioned on a table in the imaging volume of the CT imaging system. The scans of the calibration phantoms, in conjunction with air sans performed on the CT imaging system, are used to derive information about the deviation of the measured phantom scans from an ideal. The deviation information is in turn used to derive spectral calibration vectors that may be used with the CT imaging system.

17 Claims, 3 Drawing Sheets

(56) References Cited

U.S. PATENT DOCUMENTS

| | | |
|---|---|---|
| 7,280,631 B2 | 10/2007 | De Man et al. |
| 7,283,605 B2 | 10/2007 | Sainath et al. |
| 7,298,812 B2 | 11/2007 | Tkaczyk et al. |
| 7,308,073 B2 | 12/2007 | Tkaczyk et al. |
| 7,346,203 B2 | 3/2008 | Turek et al. |
| 7,379,527 B2 * | 5/2008 | Wu et al. .................. 378/18 |
| 7,382,853 B2 | 6/2008 | Arenson et al. |
| 7,391,844 B2 | 6/2008 | Wu et al. |
| 7,433,443 B1 | 10/2008 | Tkaczyk et al. |
| 7,466,793 B2 | 12/2008 | Wu |
| 7,492,855 B2 | 2/2009 | Hopkins et al. |
| 7,532,702 B2 | 5/2009 | Hsieh et al. |
| 7,570,736 B2 | 8/2009 | Hoffman et al. |
| 7,583,790 B2 | 9/2009 | Hoffman et al. |
| 7,593,502 B2 | 9/2009 | Katcha et al. |
| 7,606,347 B2 | 10/2009 | Tkaczyk et al. |
| 7,609,802 B2 | 10/2009 | Langan et al. |
| 7,613,274 B2 | 11/2009 | Tkaczyk et al. |
| 7,634,060 B2 | 12/2009 | Hoffman et al. |
| 7,697,657 B2 | 4/2010 | Walter et al. |
| 7,697,659 B2 | 4/2010 | Hoffman et al. |
| 7,724,865 B2 | 5/2010 | Wu et al. |
| 7,747,057 B2 | 6/2010 | Wu et al. |
| 7,756,239 B2 | 7/2010 | Wu et al. |
| 7,792,241 B2 | 9/2010 | Wu et al. |
| 7,801,264 B2 | 9/2010 | Wu et al. |
| 7,813,474 B2 | 10/2010 | Wu et al. |
| 7,826,587 B1 | 11/2010 | Langan et al. |
| 7,835,486 B2 | 11/2010 | Basu et al. |
| 7,869,571 B2 | 1/2011 | Hsieh et al. |
| 7,885,372 B2 | 2/2011 | Edic |
| 2004/0066911 A1 | 4/2004 | Hsieh et al. |
| 2006/0109950 A1 | 5/2006 | Arenson et al. |
| 2006/0173270 A1 | 8/2006 | Weiner et al. |
| 2006/0264749 A1 | 11/2006 | Weiner et al. |
| 2007/0124169 A1 | 5/2007 | Irving et al. |
| 2007/0147579 A1 | 6/2007 | De Man et al. |
| 2007/0147580 A1 * | 6/2007 | Wu et al. .................. 378/18 |
| 2008/0056432 A1 | 3/2008 | Pack et al. |
| 2008/0159611 A1 | 7/2008 | Tao et al. |
| 2009/0003511 A1 | 1/2009 | Roy et al. |
| 2009/0052621 A1 | 2/2009 | Walter et al. |
| 2009/0161939 A1 | 6/2009 | Wu et al. |
| 2009/0214095 A1 | 8/2009 | Wu et al. |
| 2009/0304249 A1 | 12/2009 | Wu |
| 2010/0020921 A1 | 1/2010 | Dong et al. |
| 2010/0128948 A1 | 5/2010 | Thomsen et al. |
| 2011/0026668 A1 | 2/2011 | Wu et al. |
| 2011/0052022 A1 | 3/2011 | Xu et al. |

* cited by examiner

CT SPECTRAL CALIBRATION

CROSS-REFERENCE TO RELATED APPLICATIONS

This application is a Non-Provisional of U.S. Provisional Patent Application No. 61/289,828, entitled "CT Spectral Calibration", filed Dec. 23, 2009, which is herein incorporated by reference in its entirety for all purposes.

BACKGROUND OF THE INVENTION

The subject matter disclosed herein relates to non-invasive imaging and, in particular, to spectral calibration of a radiographic imaging system.

In the fields of medical imaging and security screening, non-invasive imaging techniques have gained importance due to benefits that include unobtrusiveness, convenience, and speed. In medical and research contexts, non-invasive imaging techniques are used to image organs or tissues beneath the surface of the skin. Similarly, in industrial or quality control (QC) contexts, non-invasive imaging techniques are used to examine parts or items for hidden defects that may not be evident from an external examination. In security screening, non-invasive imaging techniques are typically used to examine the contents of containers (e.g., packages, bags, or luggage) without opening the containers and/or to screen individuals entering or leaving a secure location.

One example of a non-invasive imaging system is a computed tomography (CT) imaging system in which an X-ray source emits radiation (e.g., X-rays) towards an object or subject (e.g., a patient, a manufactured part, a package, or a piece of baggage) from a variety of different angular positions. The emitted X-rays, after being attenuated by the subject or object, typically impinge upon an array of radiation detector elements of an electronic detector, which generates signals indicate of the incident radiation at different locations on the detector. The intensity of radiation reaching the detector is typically dependent on the attenuation and absorption of X-rays through the scanned subject or object. The signals generated at the detector are processed to generate images and/or volumetric representations of the internal structures of the subject or object.

Such a CT system may be subject to various artifacts, such as beam hardening artifacts, ring/band artifacts, and/or scatter-induced artifacts. To mitigate such artifacts, a spectral calibration process may be performed using a variety of calibration phantoms. However, as the scan coverage of such CT systems has increased (particularly in the dimension extending through the imaging bore, i.e., the Z-direction), the phantoms have grown correspondingly larger to accommodate the increased scan coverage. The increased size of such calibration phantoms can make performing spectral calibrations by attaching the phantom at the edge of the patient table increasingly difficult.

BRIEF DESCRIPTION OF THE INVENTION

In one embodiment, a method for calibrating a CT system is provided. In accordance with this method, an air scan is acquired at a specified peak voltage (kVp). A phantom scan is also acquired at the kVp. The phantom scan is acquired by scanning the respective phantom on a table. Projections associated with the air scan and the phantom scan are processed with a preliminary beam hardening correction function. An image is reconstructed using the corresponding corrected projections. The image is segmented to remove non-phantom components. The segmented image is processed to generate an image pair comprising a phantom image with artifacts and a phantom image without artifacts. The image pair is projected to generate a projection pair. A respective deviation ratio is derived for the projection pair. The acquiring, processing projections, reconstructing segmenting, processing the segmented image, projecting, and deriving steps are repeated for a specified range of kVp, filters, and phantoms. A number of phantoms can be used to cover the attenuation range utilized by the CT system. Spectral calibration vectors are derived based on the respective deviation ratios.

In another embodiment, a method for acquiring phantom scan data is provided. In accordance with this embodiment, a phantom is positioned on a table and within a bore of a CT imaging system. The CT imaging system is operated to acquire projection data while the phantom is on the table and within the bore.

In a further embodiment, a method for calibrating a CT imaging system is provided. In accordance with this embodiment, a plurality of air scans are acquired at different kVp and with different filters. A plurality of phantom scans are acquired at the different kVp, with the different filters, and using different phantoms. The plurality of phantom scans are acquired with the respective phantoms positioned on a table within the field of view of the CT imaging system. The respective plurality of air scans and the respective plurality of phantom scans are processed to derive one or more spectral calibration vectors for the CT imaging system.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present disclosure provides for using large scan phantoms for performing spectral calibration of a CT imaging system. In accordance with the present approach, a phantom may be positioned on the support table during the calibration process. Contributions from the table to the acquired calibration data are removed from the calibration measurements as part of calibration process. In this manner, the CT system may undergo spectral calibration even though the calibration scan data initially includes data corresponding to other structures in addition to the calibration phantom.

With the foregoing in mind and in accordance with one embodiment, a CT imaging system is provided. The present discussion is generally provided in the context of a 3rd generation CT system, however, the present disclosure is equally applicable to other systems. For simplicity, the present discussion generally describes the use of detectors and X-ray imaging systems in a medical imaging context. However, it should be appreciated that the described radiation detectors may also be used in non-medical contexts (such as security and screening systems and non-destructive testing and/or detection systems).

Figure 1:
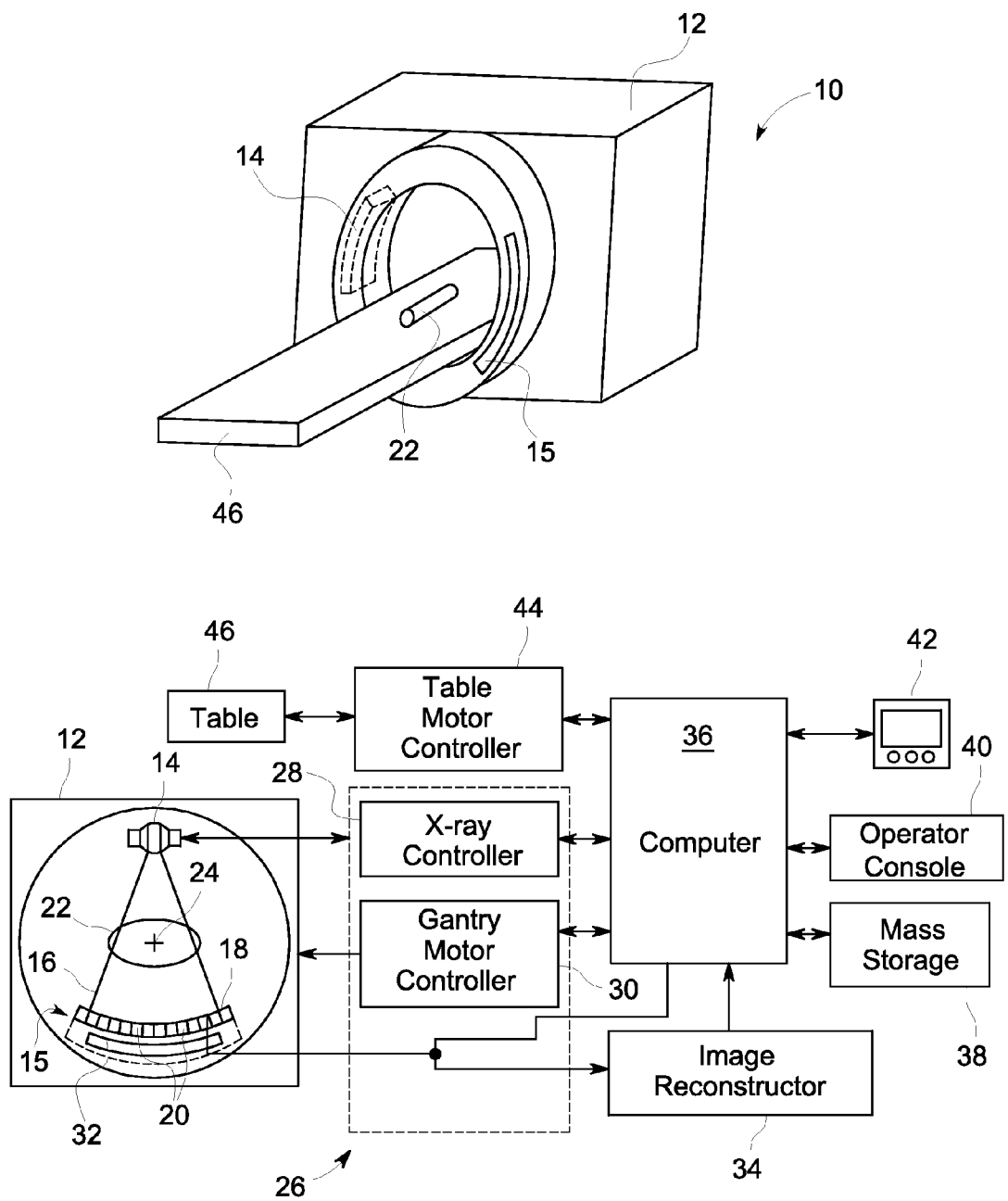
FIG. 1 is a combined pictorial view and block diagram of a CT imaging system illustrating an embodiment of the present disclosure.

Referring to FIG. 1, a computed tomography (CT) imaging system 10 is shown as including a gantry 12 representative of a "third generation" CT scanner. Gantry 12 has an X-ray source 14 that projects a beam of X-rays 16 toward a detector assembly 15 on the opposite side of the gantry 12. The detector assembly 15 includes a collimator assembly 18, a plurality of detector modules 20, and data acquisition systems (DAS) 32. The plurality of detector modules 20 detect the projected X-rays that pass through a medical patient 22, and DAS 32 converts the data to digital signals for subsequent processing. Each detector module 20 in a conventional system produces an analog electrical signal that represents the intensity of an impinging X-ray beam and hence the attenuated beam as it passes through a patient or, as depicted in FIG. 1, a spectral calibration phantom 22. During a scan to acquire X-ray projection data, gantry 12 and the components mounted thereon rotate about a center of rotation 24.

Rotation of gantry 12 and the operation of X-ray source 14 are governed by a control mechanism 26 of CT system 10. Control mechanism 26 includes an X-ray controller 28 that provides power and timing signals to an X-ray source 14 and a gantry motor controller 30 that controls the rotational speed and position of gantry 12. An image reconstructor 34 receives sampled and digitized X-ray data from DAS 32 and performs high-speed reconstruction. The reconstructed image is applied as an input to a computer 36, which stores the image in a mass storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, and gantry motor controller 30. In addition, computer 36 operates a table motor controller 44, which controls a motorized table 46 to position a patient or object undergoing imaging (e.g., the spectral calibration phantom 22, within the gantry 12. Particularly, table 46 moves portions of the subject or other object through a gantry opening 48.

Figure 2:
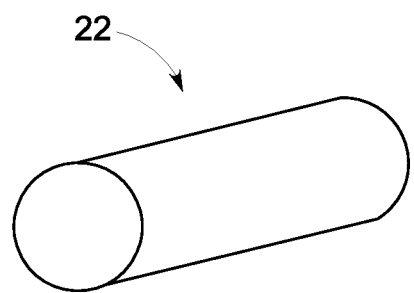
FIG. 2 depicts an example of a water-filled phantom for use in spectral calibration, in accordance with an embodiment of the present disclosure.

In conventional approaches, a CT imaging system 10 may undergo a spectral calibration process to allow for the correction or removal of soft tissue beam hardening artifacts, as well as ring/band artifacts arising from detector imperfections. In addition, the spectral calibration may allow scatter induced artifacts to be suppressed or removed. During a conventional spectral calibration process, cylindrical water phantoms (such as the generalized water phantom 22 of FIGS. 1 and 2) of various sizes are scanned to detect the deviation from an ideal projection. The measured calibration projection data through the phantoms 22 are compared with the known phantom's size and shape to compute calibration coefficients. That is the size and shape as determined from the scans of the phantoms 22 are compared to the known size and shape of the phantoms 22. In a conventional calibration scanning process, the phantoms are typically attached to a holder at the end of the patient table so that the phantom is within the scanner field of view, but the table is not within the field of view. Thus, the phantom calibration scan yields projection data which corresponds to a known shape, i.e., the phantom, without little or no contamination from other structures, such as the table 46.

However, as cone-beam CT systems have developed with increased coverage in the Z-direction, i.e., along the axis running through the imaging bore, the size of the cylindrical calibration phantoms has also increased to accommodate the extent of the increased Z-coverage. For example, a CT scanner with 40 mm coverage in the Z-direction may utilize a calibration phantom that is 80 mm long and more than 40 cm in diameter. Likewise, as Z-coverage extends to 80 mm, 320 mm and so forth, the size of the respective calibration phantoms increases correspondingly. As a result, the calibration phantoms have become so heavy that it is difficult for the phantoms to be held or suspended from the edge of the table.

As discussed herein, approaches are disclosed for scanning the calibration phantom 22 while positioned on the table 46 (as depicted in FIG. 1), without hanging or suspending the phantom 22 from the edge of the table 46. In accordance with the present approaches, the calibration vectors are computed based on the deviation of the measured projections to ideal projections from the expected known circular object (i.e., the phantom 22). In particular, ideal projections are extracted and compared with the actual or measured projections after removing the contributions from the table 46, even though the table 46 contributes to the initial measurements.

Figure 3:
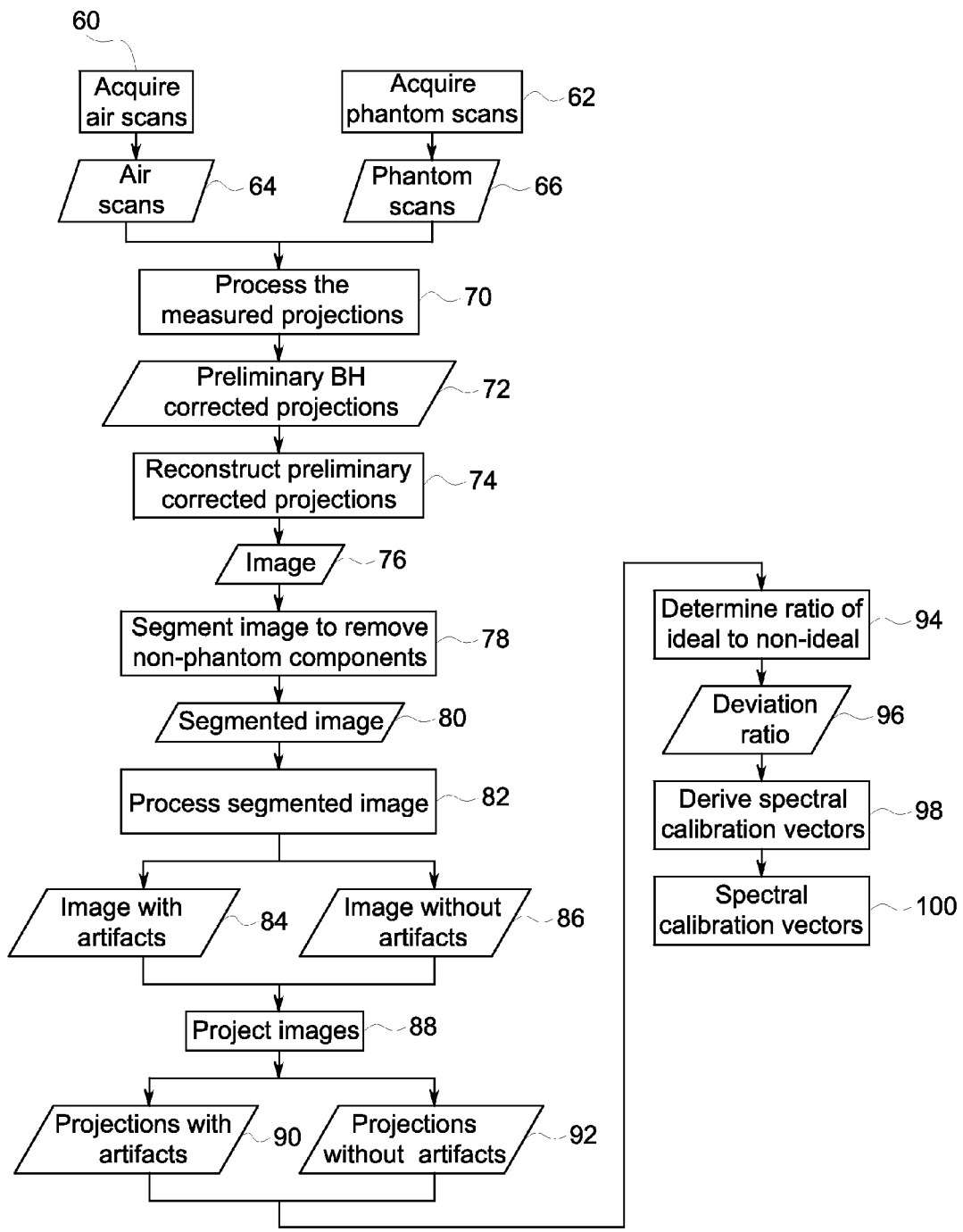
FIG. 3 depicts a flowchart of an algorithm used to derive spectral calibration vectors in accordance with the an embodiment of the present disclosure.

With the foregoing in mind, and turning now to FIG. 3, in one embodiment, respective air scans 64 and phantom scans 66 are acquired (blocks 60 and 62, respectively) at a range of kVp's (e.g., 80 kVp, 120 kVp, and 140 kVp) and with the range of available bowtie beam filters available on the scanner. For example, at a given kVp, the projections through air are measured (block 60) without the patient table 46 in the beam. The phantom calibration scans (block 62) are typically performed using multiple cylindrical water or water-like objects of different sizes (e.g., phantoms) placed in the beam path. The phantoms 22 are placed on the table 46 and scanned at the given kVp. The respective air and phantom scans (blocks 60 and 62) are repeated for all the kVp's and bowtie beam filters offered by the scanner and a determined dark current value is subtracted from the generated data. The data collected by these calibration scans includes the air scans 64 acquired at different kVp's and with different bowtie filters and the phantom scans 66 acquired at different kVp's, with different bowtie filters, and using a range of differently sized phantoms 22. In one embodiment, the phantoms 22 can be centered or off-centered with respect to the iso-center of the scanner, e.g., imaging system 10. Thus, after data collection, the following data is available for subsequent processing: air scans (i.e., $a_D$), which correspond to the air profile, with dark current subtracted, at a given kVp and bowtie filtration, where D is the detector index in x-direction; and phantom scans (i.e., $w_D^d$), which correspond to the raw data through water attenuation of a diameter d circular phantom, with dark current subtracted, at corresponding kVp and bowtie filtration as in the respective air scan.

After data collection, deviations from the expected values are determined. As will be appreciated, when the table 46 is present in the X-ray beam, the measured projections can be of un-controlled shape. It is presumed that one does not have a direct expectation of these projections that represent the ideal case and free of artifacts attributable to detector imperfections and beam hardening. However, in a successfully calibrated system, the phantom should be uniform at the targeted Hounsfield units (HU) value.

In the measurement, the table 46 should contribute little to the attenuation compared to the phantom 22. Therefore, it would be a reasonable approximation that the deviations from the ideal condition in the image reconstructed with preliminary beam hardening correction vectors, which can be computed theoretically, would be contributed mostly by the phantom 22. With this assumption, a new pair of physical and ideal projections can be obtained by processing (block 70) the measured projections $p_D^d$ in accordance with:

$$p_D^d = -\log\left(\frac{w_D^d}{a_D}\right) \quad (1)$$

$$p_D^d = f_D(p_D^d)$$

Where, $f_D(\ )$ is the preliminary beam hardening correction functional form, mostly in the polynomial format.

In one implementation, the preliminary beam hardening corrected projections 72 are reconstructed (block 74) to form an image 76 (i.e., Ig(x, y)). The image 76 may not be fully corrected and may include rings/bands and/or HU differences (i.e., non-uniformities) in the phantom (e.g., water) region. The phantom cylinder in image Ig(x, y) is segmented (block 78), eliminating the table 46 and any other non-phantom components from the image 76. The segmented image 80 may be processed (block 82) to represent the ideal image by setting the phantom (e.g., water) HU value to the targeted value, e.g., 1000, yielding pairs of phantom (e.g., water cylinder) images, one image 84 (i.e., Ig(x', y')) with artifacts, and one image 86 (i.e., Ig$_{ideal}$(x', y')) without artifacts. Such processing may be threshold-based, taking advantage of the relatively weak attenuation provided by the table in comparison to the water in the phantom.

The paired images 84, 86 (i.e., Ig(x', y') and Ig$_{ideal}$(x', y')) are forward projected (block 88) to the same ray path as the corresponding measured projections $p_D^d$, resulting in paired projection sets 90, 92 (i.e., $pf_D^d$, $pf_{D,ideal}^d$). The deviation of the projection from the ideal value for each phantom is described (block 94) by the deviation ratio 96:

$$r_D^d = \frac{pf_{D,ideal}^d}{pf_D^d} \quad (2)$$

at a total projection (uncorrected) value of $p_D^d$. With a reasonably good preliminary calibration vector set, the computed deviation ratio 96 (i.e., $r_D^d$) describes the characteristic of the CT detection system, with a value typically close to 1.0. This procedure is repeated for all the phantom sizes, indexed by d. In one implementation, three to four phantoms are used to fully cover the calibration range.

For a given detector index, D, the spectral calibration vectors 100 can be obtained (block 98) by combining the preliminary beam hardening correction functions and the deviation ratio 96 (i.e., $r_D^d$) from all phantoms 22, i.e., by updating the beam hardening correction functions with the extracted deviations from the ideal. For example, in one embodiment, correction data pairs are generated using the preliminary beam hardening correction for projection values covering a range of interest, such as:

$$(p, f_D(p)) \quad (3)$$

where p ranges from 0 to 12.0, with a step of 0.2. In addition, data points are generated using the phantom measurements such that each phantom measurement (e.g., 3 or 4 phantom measurements) yield a set of data pairs that can be used to generate an ideal phantom image (e.g., water image) free of artifacts. For example, in one embodiment these data sets are generated as:

$$p_D^d, f_D(p_D^d) \cdot r_D^d \quad (4)$$

where $r_D^d$ provided the desired correction.

The data pair points generated using the preliminary beam hardening correction and those generated from the phantom measurement are combined to include both the correction provided by preliminary calibration vectors and additional correction from measurements. The data pairs from the preliminary calibration are included to confine the fitting to follow the trend of the functional curve. The new data pair sets can be expressed as:

$$\{p_D^d; p \to f_D(p); f_D(p_D^d) \cdot r_D^d\}. \quad (5)$$

In one implementation, the above data pairs are fitted with the designated functional form for the spectral calibration. In one embodiment, more weight is given to the data pairs deduced from measurements (that is the data pairs deduced in accordance with equation (4). In the polynomial format, the data sets are fitted with a polynomial form, such as a 3rd to 4th order form, resulting in typically calibration vectors 100 (e.g., a1, a2, a3, aN), satisfying:

$$(f_D(p); f_D(p_D^d) \cdot r_D^d) = a_1 \cdot (p; p_D^d) + a_2 \cdot (p; p_D^d)^2 + a_3 \cdot (p; p_D^d)^3 \quad (6)$$

The new calibration vectors are used as the preliminary beam hardening correction, as depicted at block 70, and the process is iterated a set number of times, until a cost or other threshold function is satisfied, or until a satisfactory calibration vectors (as determined by any suitable criteria) are obtained for all the detector cells in the system. Thus, as discussed above, the algorithm discussed herein provides a way to perform spectral calibration for a CT system with phantoms placed directly on the patient table, without requiring precise phantom centering.

Technical effects of the invention include spectral calibration of a CT system using a phantom that is scanned while on the patient table. Other technical effects include removing non-phantom contributions from calibration scan data to facilitate calibration of an imaging system. Additional technical effects include deriving a deviation ratio describing the deviation of a set of measured calibration projections from corresponding set of ideal calibration projections and calculating calibration vectors using the deviation ratio.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for calibrating a CT system, comprising:
   acquiring an air scan at a specified peak voltage (kVp);
   acquiring a phantom scan at the kVp, wherein the phantom scan is acquired by scanning the respective phantom on a table;
   processing projections associated with the air scan and the phantom scan with a preliminary beam hardening correction function;
   reconstructing an image using the corresponding corrected projections;
   segmenting the image to remove non-phantom components;
   processing the segmented image to generate an image pair comprising a phantom image with artifacts and a phantom image without artifacts;
   projecting the image pair to generate a projection pair;
   deriving a respective deviation ratio for the projection pair;

repeating the acquiring, processing projections, reconstructing segmenting, processing the segmented image, projecting, and deriving steps for a specified range of kVp, filters, and phantoms covering the attenuation range of the CT system; and deriving spectral calibration vectors based on the respective deviation ratios.

2. The method of claim 1, wherein projecting the image pair comprises forward projecting the image pair along the same ray path as the corresponding measured projections.

3. The method of claim 1, wherein the deviation ratios each comprise the ratio of an ideal projection over a measured projection.

4. The method of claim 1, wherein the kVp's are at 80 kVp, 120 kVp, and 140 kVp.

5. The method of claim 1, wherein the phantoms are water-filled cylinders.

6. The method of claim 1, wherein segmenting the image comprises segmenting the image based on one or more threshold intensities.

7. The method of claim 1 wherein processing the segmented image comprises setting one or more intensity values within a segment corresponding to the phantom to a target value associated with the phantom.

8. The method of claim 1, comprising updating the preliminary beam hardening correction function with the derived spectral calibration vectors and iterating the remaining steps.

9. A method for calibrating a CT imaging system, comprising:

acquiring a plurality of air scans at different kVp and with different filters;

acquiring a plurality of phantom scans at the different kVp, with the different filters, and using different phantoms, wherein the plurality of phantom scans are acquired with the respective phantoms positioned on a table within the field of view of the CT imaging system;

processing the respective plurality of air scans and the respective plurality of phantom scans to derive one or more spectral calibration vectors for the CT imaging system.

10. The method of claim 9, wherein processing the respective plurality of air scans and the respective plurality of phantom scans comprises:

processing projections associated with respective air scans and the phantom scans with respective preliminary beam hardening correction functions;

reconstructing a plurality of images using the corresponding corrected projections;

segmenting the images to remove non-phantom components;

processing the segmented images to generate image pairs each comprising a phantom image with artifacts and a phantom image without artifacts;

projecting the respective image pairs to generate respective projection pairs;

deriving a respective deviation ratio for each projection pair; and deriving the spectral calibration vectors based on the respective deviation ratios.

11. The method of claim 9, wherein projecting the respective image pairs comprises forward projecting each image pair along the same ray path as the corresponding measured projections.

12. The method of claim 9, wherein the deviation ratios each comprise the ratio of an ideal projection over a measured projection.

13. The method of claim 9, wherein the phantoms are water-filled cylinders.

14. The method of claim 9, wherein segmenting the images comprises segmenting the images based on one or more threshold intensities.

15. The method of claim 9, wherein processing the segmented image comprises setting one or more intensity values within a segment corresponding to a respective phantom to a target value associated with the respective phantom.

16. The method of claim 9, wherein comprising updating the preliminary beam hardening correction function with the derived spectral calibration vectors.

17. The method of claim 9, wherein the kVp's are at 80 kVp, 120 kVp, and 140 kVp.

* * * * *